(12) United States Patent
Halalay et al.

(10) Patent No.: US 7,940,060 B2
(45) Date of Patent: May 10, 2011

(54) METHOD FOR MEASURING THE AMOUNT OF AIR IN A FLUID

(75) Inventors: Ion C. Halalay, Grosse Pointe Park, MI (US); Eric W. Schneider, Shelby Township, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 0 days.

(21) Appl. No.: 11/682,345

(22) Filed: Mar. 6, 2007

(65) Prior Publication Data

US 2008/0218325 A1 Sep. 11, 2008

(51) Int. Cl.
*G01R 27/08* (2006.01)
(52) U.S. Cl. ..... 324/698; 73/19.01; 73/19.11; 73/304 C; 123/196 R
(58) Field of Classification Search ............ 324/698
See application file for complete search history.

(56) References Cited

U.S. PATENT DOCUMENTS

| | | | | |
|---|---|---|---|---|
| 4,599,888 | A * | 7/1986 | Hufton et al. ........... | 73/19.11 |
| 4,820,973 | A * | 4/1989 | Alvarez .................. | 73/304 C |
| 6,758,187 | B2 * | 7/2004 | Waters ..................... | 123/198 F |
| 6,844,745 | B1 * | 1/2005 | Schachameyer et al. ... | 324/698 |
| 2004/0149032 | A1 * | 8/2004 | Sell .......................... | 73/304 C |
| 2004/0244501 | A1 * | 12/2004 | Nyfors et al. ............ | 73/861.63 |
| 2005/0248358 | A1 * | 11/2005 | Boyle et al. .............. | 324/698 |
| 2006/0232267 | A1 * | 10/2006 | Halalay et al. ........... | 324/158.1 |

FOREIGN PATENT DOCUMENTS

EP 448892 A2 * 10/1991

OTHER PUBLICATIONS

Nelson, S.O.; Pemittivity and Density Relationships for Granular and Powdered Materials, Antennas and Propagation Society International Symposium, 2004. IEEE vol. 1, Jun. 20-25, 2004 pp. 229-232.*
G. T. Waby, An Aeration Meter for Lubricating Oils, J. Sci. Instrum. 1965, vol. 42, pp. 425-427.

* cited by examiner

*Primary Examiner* — Timothy J Dole
*Assistant Examiner* — Benjamin M Baldridge
(74) *Attorney, Agent, or Firm* — Reising Ethington P.C.

(57) ABSTRACT

One embodiment of the invention includes a method comprising measuring the level of a fluid in a system in a vehicle comprising measuring an electrical property of the fluid indicative of the amount of air in the fluid and comparing the measured electrical property to a reference. The measured electrical property may include at least one of electrical resistivity or electrical permittivity. Another embodiment of the invention includes a method comprising measuring an electrical property of a fluid, measuring an electrical property of an air-free fluid sample, and determining a volume fraction of air in the fluid using the electrical property of the fluid and the electrical property of the air-free fluid sample, wherein the electrical property comprises at least one of electrical resistivity or electrical permittivity. In some embodiments an indication can be provided when the slope of the electrical property versus time changes.

11 Claims, 7 Drawing Sheets

FIG. 7

METHOD FOR MEASURING THE AMOUNT OF AIR IN A FLUID

TECHNICAL FIELD

The field to which the disclosure generally relates includes methods for measuring properties of a fluid.

BACKGROUND

Inadequate lubrication of the engine in a vehicle due to a low oil level can cause engine damage and failure. Moreover, oil aeration can have many other adverse consequences. A decrease in oil pressure may cause bearing wear or failure. An increase in compressibility may cause loss of capability as a hydraulic fluid. Excessive aeration at shut-down may lead to valve train noise during subsequent start-up.

SUMMARY OF EXEMPLARY EMBODIMENTS OF THE INVENTION

One embodiment of the invention includes a method comprising measuring the level of a fluid in a system in a vehicle comprising measuring an electrical property of the fluid indicative of the amount of air in the fluid; and comparing the measured electrical property to a reference.

Other exemplary embodiments of the invention will become apparent from the detailed description of exemplary embodiments provided hereinafter. It should be understood that the detailed description and specific examples, while indicating the exemplary embodiments of the invention, are intended for purposes of illustration only and are not intended to limit the scope of the claimed invention.

BRIEF DESCRIPTION OF THE DRAWINGS

Exemplary embodiments of the invention will become more fully understood from the detailed description and the accompanying drawings.

DETAILED DESCRIPTION OF EXEMPLARY EMBODIMENTS

The following description of the embodiments is merely exemplary in nature and is in no way intended to limit the claimed invention, its application, or uses.

Figure 1:
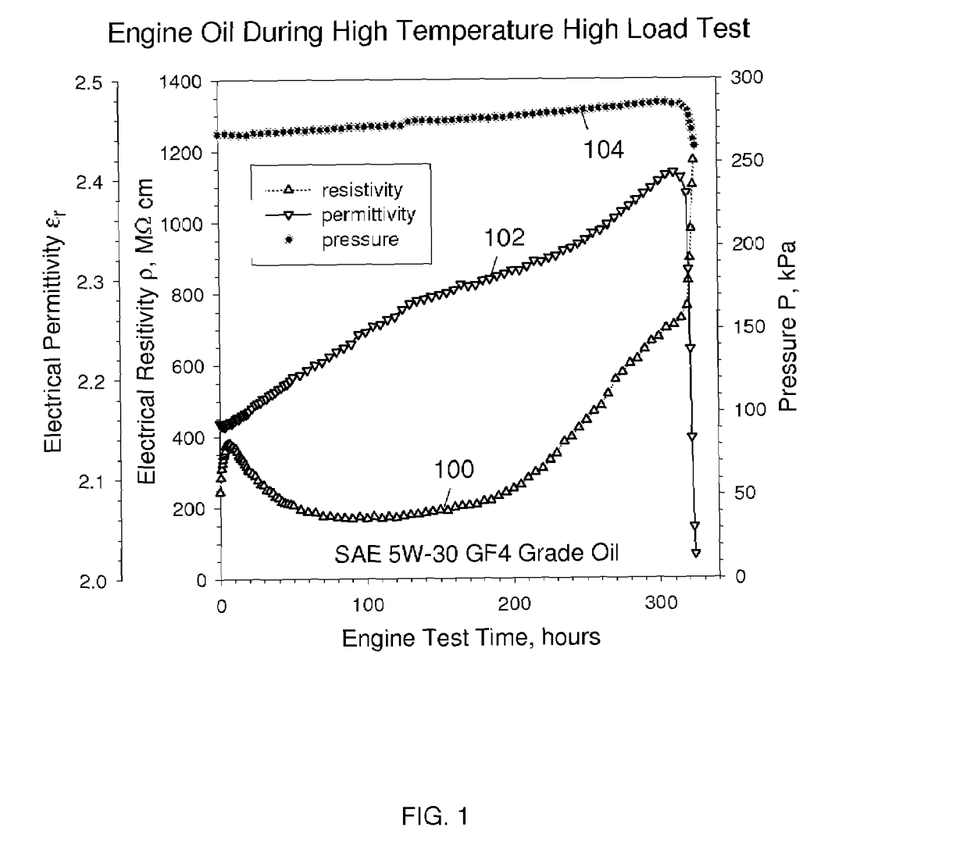
FIG. 1 is a plot of electrical permittivity, electrical resistivity, and pressure of an oil over time during an engine dynamometer test.
Figure 2:
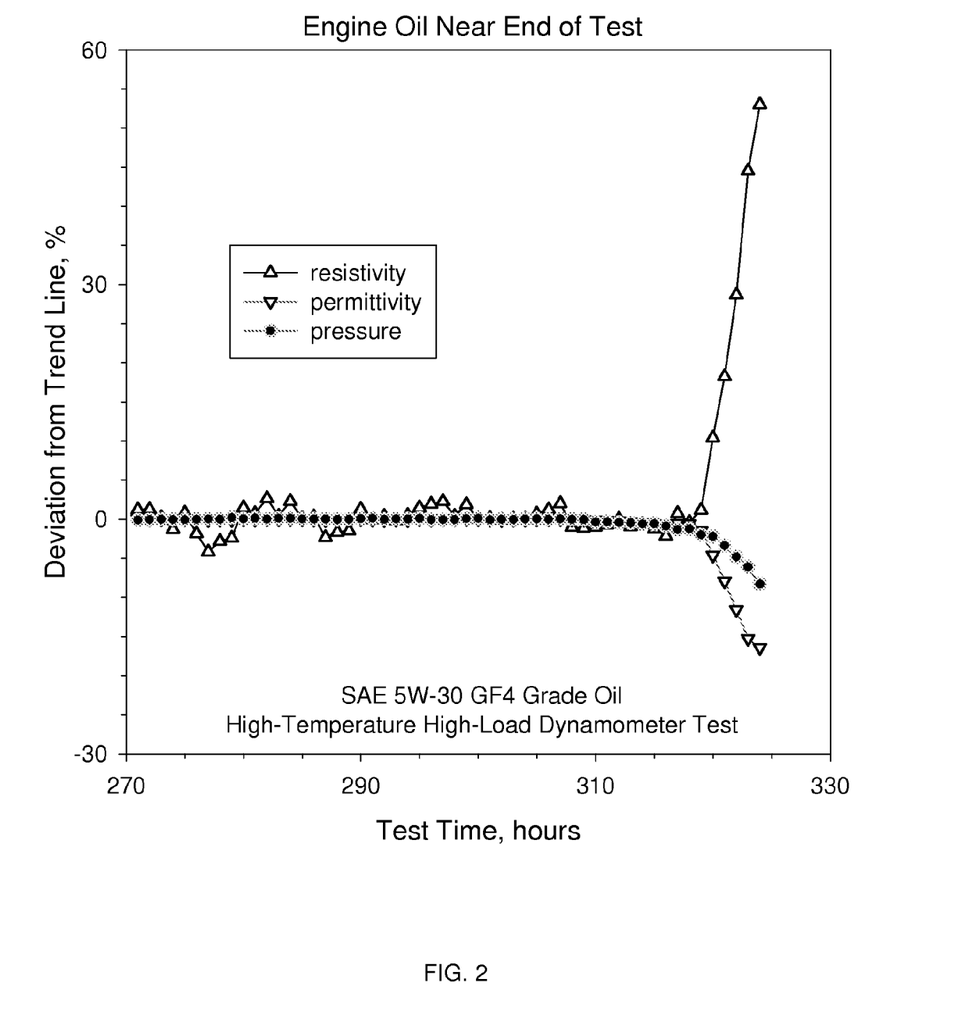
FIG. 2 is a plot of the percent change from the respective trend lines for electrical permittivity, electrical resistivity, and pressure of an oil over time during an engine dynamometer test.

FIG. 1 illustrates the change in electrical resistivity 100, electrical permittivity 102, and pressure 104 of an oil over time during an engine oil test using a commercial SAE 5W-30, GF4 quality, mineral-based engine oil. The test was a high temperature high load (HTHL) engine dynamometer test. After approximately 310 hours of the test, the engine oil became aerated due to an excessively low engine oil level in the pan. FIG. 2 illustrates the deviation from the trend line for electrical resistivity 100, electrical permittivity 102, and pressure 104 of an engine oil during the last 60 hours of the HTHL engine dynamometer test illustrated in FIG. 1. As shown in FIG. 2, the changes produced by aeration in the measured electrical resistivity 100, electrical permittivity 102, and oil pressure 104 during the last 5 hours of the test were approximately 50%, 20%, and 10%, respectively. Therefore, the electrical resistivity 100 and the electrical permittivity 102 are more sensitive than the oil pressure 104 to engine oil aeration.

Figure 3:
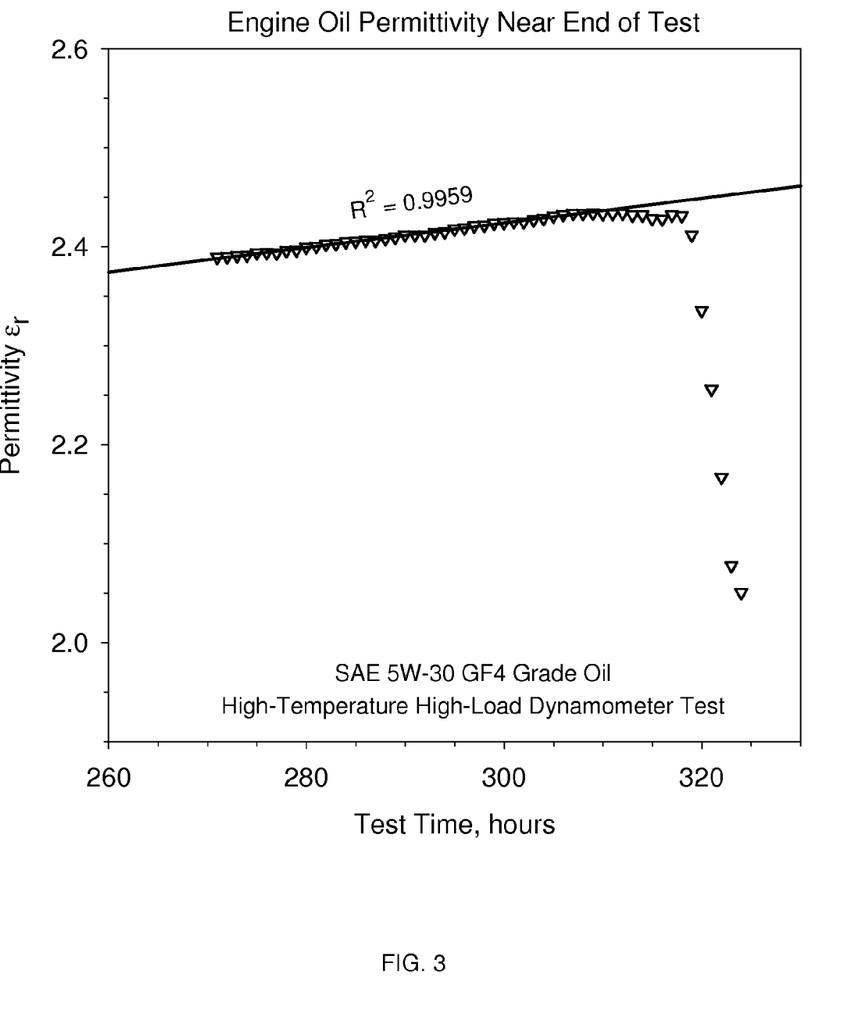
FIG. 3 is a plot of the electrical permittivity of an oil over time during an engine dynamometer test.

FIG. 3 illustrates the sharp decline in electrical permittivity at the end of the test. In one embodiment of the invention, the decrease in electrical permittivity may be an indicator of a low engine oil level. When the oil level in the sump drops below a certain level, air begins to be drawn in the oil pick-up tube and oil aeration begins to occur. Air is a low permittivity component because the electrical permittivity of air is approximately 1 and the electrical permittivity of hydrocarbon fluids is approximately 2 or greater. For example, the electrical permittivity of engine oil is approximately 2 to 3. Therefore, the addition of air to the engine oil results in a lower electrical permittivity for the mixture.

Figure 4:
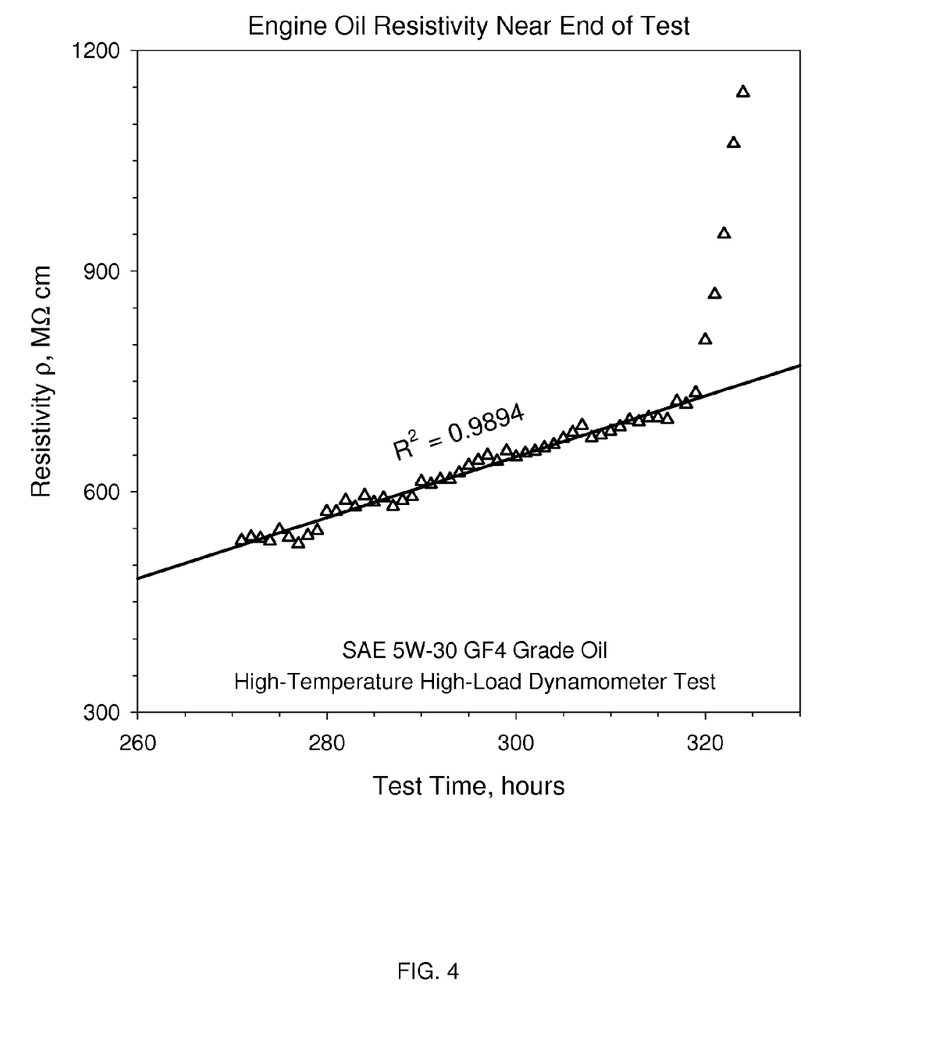
FIG. 4 is a plot of the electrical resistivity of an oil over time during an engine dynamometer test.

FIG. 4 illustrates the sharp increase in electrical resistivity of the engine oil at the end of the HTHL engine dynamometer test from FIG. 1. In one embodiment of the invention, the increase in electrical resistivity may be an indicator of low engine oil levels. When the oil level in the sump drops below a certain level, air begins to be drawn in the oil pick-up tube and oil aeration begins to occur. Air is an electrical insulator, so the measured increase in electrical resistivity is due to the reduction of the cross-sectional area of the cell that is available for electrical conduction.

Figure 5:
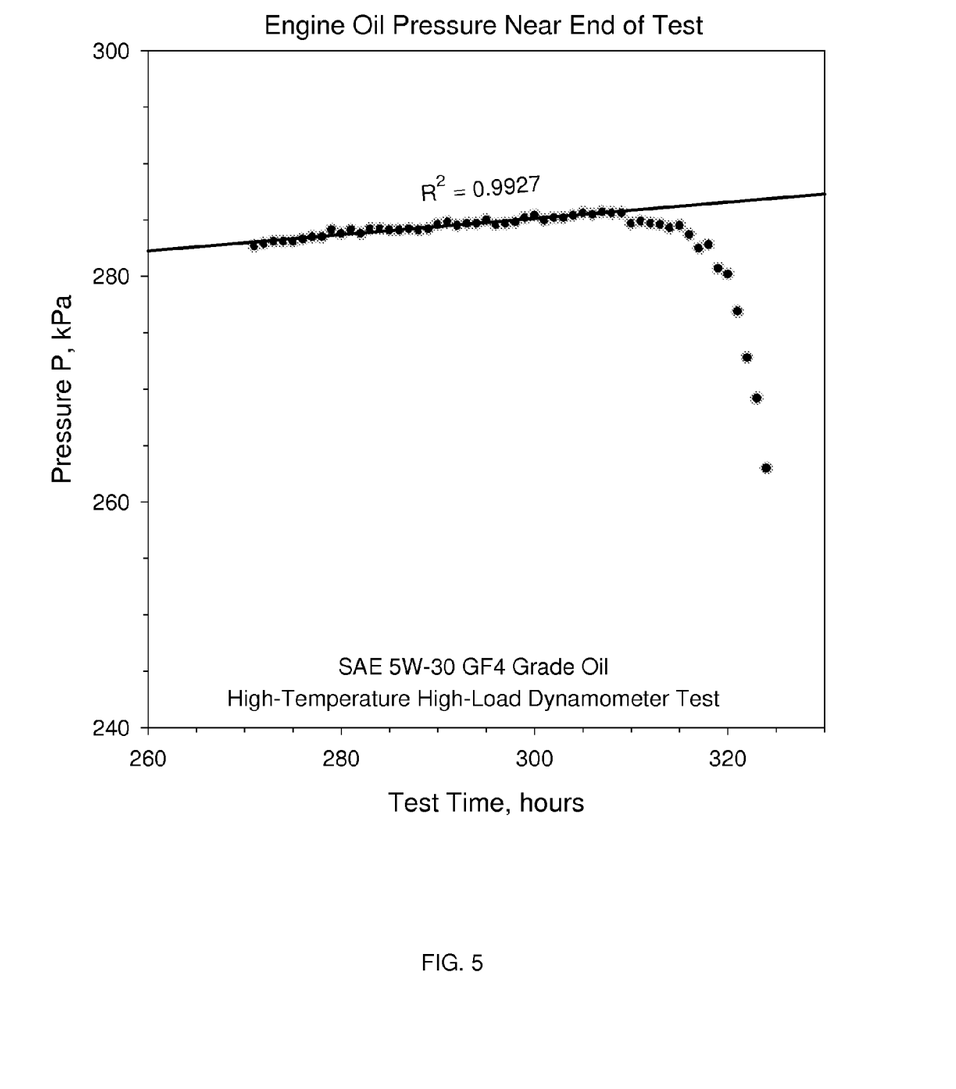
FIG. 5 is a plot of oil pressure over time during an engine dynamometer test.

FIG. 5 illustrates the decline in the pressure of the engine oil at the end of the HTHL engine dynamometer test from FIG. 1.

In one embodiment, detection of a low level in a fluid in a vehicle, for example engine oil, transmission fluid, brake fluid, engine coolant, ionic liquid, or another fluid, can be performed by monitoring deviations of the measured values of the electrical resistivity and electrical permittivity from their respective trend lines.

The amount of air in a fluid, for example engine oil, transmission fluid, brake fluid, engine coolant, ionic liquid, or another fluid, can be determined from electrical permittivity, using one of several mixing rules for the permittivity. For two fluids that do not vary much in their permittivities, as is the case for hydrocarbons and air, the Landau-Lifschitz-Looyenga equation was shown to provide the most accurate values for the permittivity of their mixture:

$$\epsilon_{mix}^{1/3} = \phi_{oil}\epsilon_{oil}^{1/3} + \phi_{air}\epsilon_{air}^{1/3}$$

For example, where the fluid is engine oil, $\epsilon_{mix}$ is the electrical permittivity of the engine oil, $\epsilon_{oil}$ is the electrical permittivity of an air-free engine oil sample, $\epsilon_{air}$ is 1 to a very good approximation ($\epsilon_{air}=1.00059\approx1$ to within 0.06%), $\phi_{air}$ is the volume fraction of air in oil, and $\phi_{oil}=1-\phi_{air}$. In one embodiment, the electrical permittivity of an air-free reference engine oil, $\epsilon_{oil}$ is measured by a reference sensor. The electrical permittivity of the engine oil, $\epsilon_{mix}$, is measured by a test sensor. In one embodiment, the reference sensor and the test sensor are electrical ac impedance sensors located in the two branches of an oil bypass line. The test sensor may measure the electrical permittivity of the air-containing engine oil, $\epsilon_{mix}$, in real time while the engine is running. The volume fraction of air in the oil, $\phi_{air}$, may then be determined using the above Landau-Lifschitz-Looyenga equation. In another embodiment, the volume fraction of air in the oil, $\phi_{air}$, may be determined through an alternative empirical calibration procedure.

In one embodiment, a reference cell may contain an approximately air-free first reference fluid, for example engine oil. A vacuum may be applied to the reference cell to remove air bubbles from the first reference engine oil, and the electrical permittivity of the air-free first reference engine oil, $\epsilon_{oil}$, may be measured. As the (non-reference) engine oil degrades over time, the electrical permittivity of the engine oil may change. In one embodiment, after a certain period of time, the reference cell may be emptied of the first reference engine oil. The reference cell may be refilled with the degraded (aged) engine oil, which serves as a second reference engine oil. Then a vacuum may be re-applied to remove the air from the second reference engine oil in the reference cell. The electrical permittivity of the second reference engine oil may be measured. This procedure may be repeated when necessary, as dictated by the rate of degradation of the oil. The reference cell may be located in a vehicle. The electrical permittivity may be measured when the engine has reached a suitable operating temperature.

Figure 6:
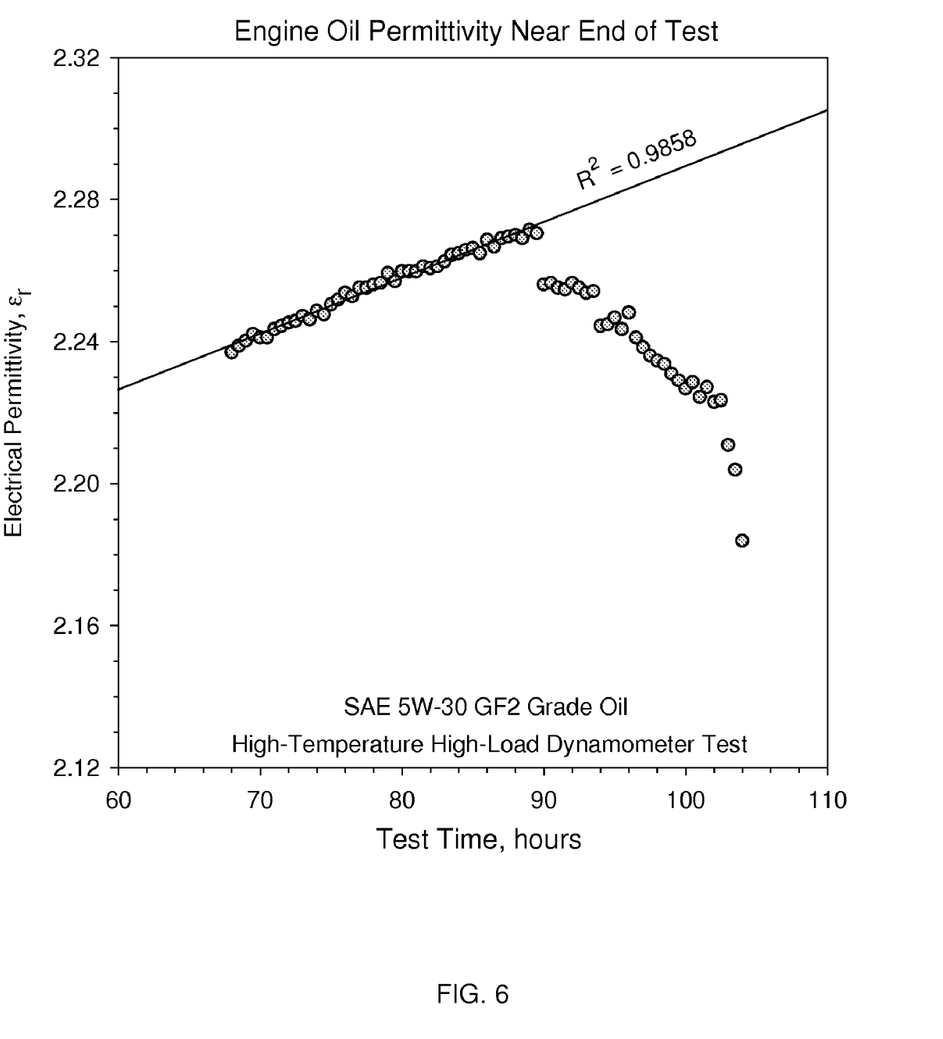
FIG. 6 is a plot of the electrical permittivity of an oil over time during an engine dynamometer test.
Figure 7:
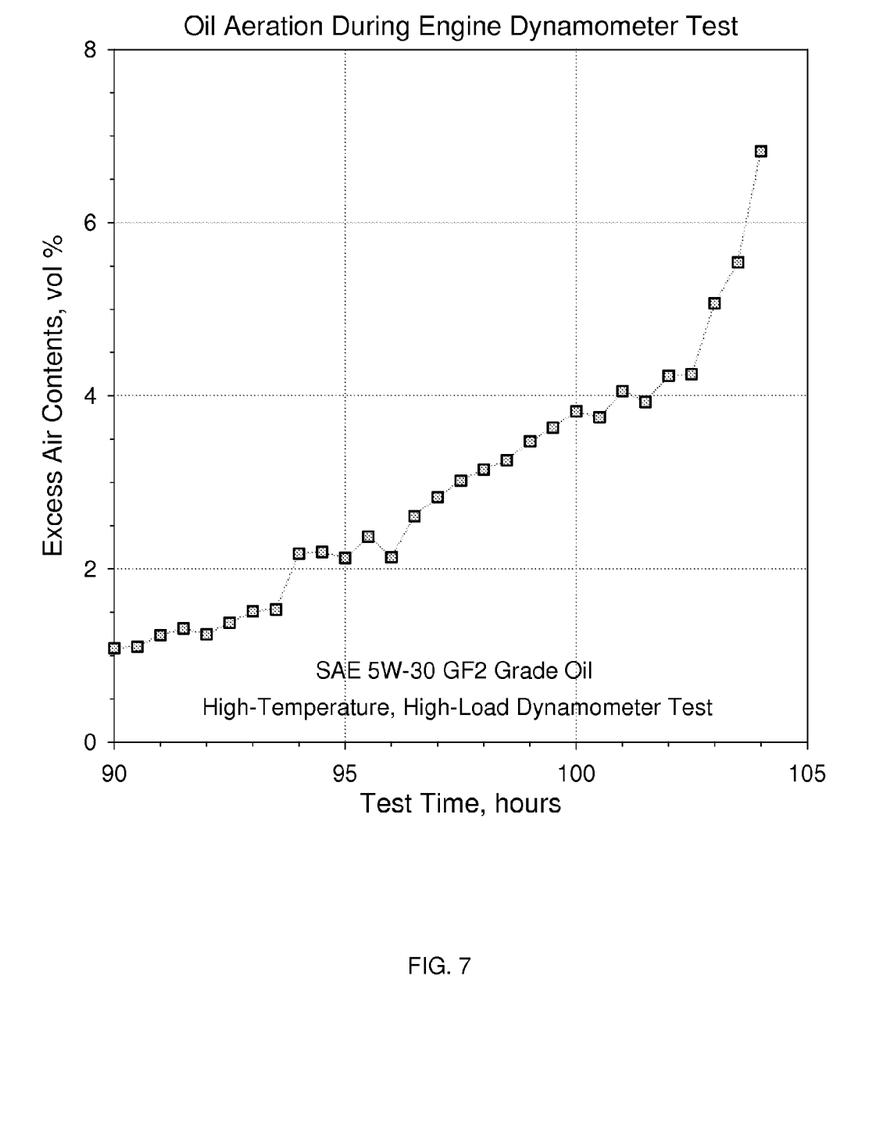
FIG. 7 is a plot of the excess air content in an engine oil, in volume percent, over time during an engine dynamometer test.

FIG. 6 illustrates the electrical permittivity over time during an HTHL dynamometer test for a commercial, GF-2 quality, SAE 5W-30 mineral-based engine oil. FIG. 7 illustrates the amount of excess air in the oil, by percent volume of air in the engine oil, over the test time for the HTHL dynamometer test illustrated in FIG. 6. The amount of excess air was estimated based on the measured electrical permittivity using the Landau-Lifschitz-Looyenga equation.

An increase in oil aeration may provide a signal that the engine oil level is low and that oil needs to be added. An adequate level of oil is needed to maintain oil pressure and protect engine bearings. In addition, the aeration signal may also warn of other types of engine malfunction and damage. For example, oil aeration leads to an increase in oil compressibility, which may adversely affect the capability of oil as a hydraulic fluid for valve train control. Excessive oil aeration at shutdown may also cause valve train noise during subsequent engine startup.

In one embodiment, at least one electrical property of a fluid is repeatedly measured over time. The slope of the electrical property versus time curve, or the product of two electrical properties versus time curve, is calculated repeatedly. When the slope exhibits a first change, an indication may be provided. For example, the first change may be a change from positive to negative. The first change may also be a significant deviation from the previous slope, for example at least a ten percent deviation. The electrical property measured may include at least one of electrical permittivity and electrical resistivity.

In another embodiment, the electrical permittivity of a fluid, for example engine oil, is measured over time and the slope of the electrical permittivity versus time curve is calculated. The permittivity of a fluid may vary with temperature. When the slope of the electrical permittivity versus time curve changes from positive to negative, an indication is provided, The indication may be a warning light in a vehicle. For example, the driver of a vehicle may be warned by an "ADD OIL" warning light when the engine oil level drops below a certain critical level. The critical level may correspond to a certain decrease in electrical permittivity caused by aeration of the engine oil.

In another embodiment, the electrical resistivity of a fluid, for example engine oil, is measured over time and the slope of the electrical resistivity versus time curve is calculated. When the slope of the electrical resistivity versus time curve increases significantly, an indication is provided. The indication may be a warning light in a vehicle. For example, the driver of a vehicle may be warned by an "ADD OIL" warning light when the engine oil level drops below a certain critical level. The critical level may correspond to a certain increase in electrical resistivity caused by aeration of the engine oil above what is expected during normal engine operation.

In another embodiment, the electrical permittivity and the electrical resistivity of a fluid, for example engine oil, is measured over time and the slope of the product of the electrical permittivity and electrical resistivity is calculated. When the slope of the product of the electrical permittivity and electrical resistivity versus time curve changes from positive to negative, an indication is provided. The indication may be a warning light in a vehicle. For example, the driver of a vehicle may be warned by an "ADD OIL" warning light when the engine oil level drops below a certain critical level.

In one embodiment, the electrical permittivity of a fluid, such as an engine oil, transmission fluid, brake fluid, engine coolant, ionic liquid, or another fluid, is measured over time and compared to a predetermined target range under certain operating conditions of the vehicle. If the measured electrical permittivity is outside the target range, an indicator is provided. The predetermined target range may be determined using a reference (for example from an air-free sample), calculated, estimated, obtained from a look-up table, and the like.

In one embodiment, the electrical resistivity of a fluid, such as an engine oil, transmission fluid, brake fluid, engine coolant, ionic liquid, or another fluid, is measured over time and compared to a predetermined target range under certain operating conditions of the vehicle. If the measured electrical resistivity is outside the target range, an indicator is provided. The predetermined target range may be determined using a reference (for example from an air-free sample), calculated, estimated, obtained from a look-up table, and the like.

Embodiments of the invention may be used to rapidly evaluate engine hardware designs and lubricant formulations that minimize oil aeration during specific engine operating conditions.

The above description of embodiments of the invention is merely exemplary in nature and, thus, variations thereof are not to be regarded as a departure from the spirit and scope of the invention.

What is claimed is:

1. A method comprising:
   measuring an electrical property of a fluid;
   measuring an electrical property of an air-free fluid sample; and
   determining a volume fraction of air in the fluid using the electrical property of the fluid and the electrical property of the air-free fluid sample, wherein the determining the volume fraction of air in the fluid comprises applying a mixing rule for the permittivity, and wherein the electrical property comprises at least one of electrical resistivity or electrical permittivity, wherein the fluid is selected from the group consisting of engine oil, transmission fluid, brake fluid, engine coolant, and ionic liquid.

2. A method as set forth in claim 1 wherein the mixing rule for the permittivity is the Landau-Lifschitz-Looyenga mixing rule for the permittivity.

3. A method as set forth in claim 1 further comprising measuring the electrical property of the fluid in real time in a vehicle while an engine of the vehicle is running.

4. A method as set forth in claim 1 wherein the electrical property comprises electrical permittivity and the measuring the electrical permittivity comprises using electrical ac impedance sensors.

5. A method as set forth in claim 1 further comprising using the volume fraction of air in the fluid to evaluate an engine design based on oil aeration.

6. A method as set forth in claim 1 wherein the fluid is a liquid, and wherein the air-free fluid sample is an air-free liquid sample.

7. A method comprising:
  measuring an electrical property of a fluid;
  measuring an electrical property of an air-free fluid sample; and
  determining a volume fraction of air in the fluid using the electrical property of the fluid and the electrical property of the air-free fluid sample, wherein the electrical property comprises electrical permittivity and the measuring the electrical permittivity comprises using electrical ac impedance sensors, and wherein the electrical ac impedance sensors are provided in two branches of an oil bypass line.

8. A method for detecting and indicating the presence of an undesirable amount of air in a fluid comprising:
  repeatedly measuring at least one electrical property of a fluid over time, wherein the electrical property comprises electrical permittivity or a product of electrical permittivity and electrical resistivity;
  repeatedly calculating a slope of a curve representing the electrical property versus time;
  providing an indication when the slope changes from positive to negative, indicating an undesirable amount of air in the fluid.

9. A method as set forth in claim 8 wherein the fluid is selected from the group consisting of engine oil, transmission fluid, brake fluid, engine coolant, and ionic liquid.

10. A method as set forth in claim 8 wherein the indication comprises a warning light indicative of a low fluid level in a vehicle when the slope changes from positive to negative.

11. A method of quantitatively determining an undesirable amount of air in a fluid comprising:
  measuring the permittivity of the fluid;
  estimating the air fraction in a fluid from the measured permittivity value in the current state of the fluid and a known permittivity value for the air-free fluid;
  comparing the estimated air fraction in the fluid to a predetermined target range for a vehicle; and
  providing an indication when the estimated air fraction is outside of the predetermined target range, wherein the indication comprises a warning light in the vehicle or an audible signal or message.

* * * * *